US011583519B2

(12) United States Patent
    Popov

(10) Patent No.: US 11,583,519 B2
(45) Date of Patent: *Feb. 21, 2023

(54) NASAL COMPOSITIONS AND METHOD OF USE THEREOF

(71) Applicant: Nasaleze Patents Limited, Isle of Man (GB)

(72) Inventor: Todor A. Popov, Sofia (BG)

(73) Assignee: Nasaleze Patents Limited, Isle of Man (GB)

( * ) Notice: Subject to any disclaimer, the term of this patent is extended or adjusted under 35 U.S.C. 154(b) by 351 days.

This patent is subject to a terminal disclaimer.

(21) Appl. No.: 16/657,501

(22) Filed: Oct. 18, 2019

(65) Prior Publication Data
US 2020/0054609 A1    Feb. 20, 2020

Related U.S. Application Data

(63) Continuation of application No. 15/317,211, filed as application No. PCT/GB2015/051661 on Jun. 8, 2015.

(30) Foreign Application Priority Data

Jun. 10, 2014    (GB) ..................... 1410250

(51) Int. Cl.
    A61K 47/38        (2006.01)
    A61K 9/14         (2006.01)
    (Continued)

(52) U.S. Cl.
    CPC .......... *A61K 31/4174* (2013.01); *A23L 33/10* (2016.08); *A61K 9/0043* (2013.01);
    (Continued)

(58) Field of Classification Search
    CPC .............. A61K 31/4174; A61K 9/0043; A61K 9/0075; A61K 9/1652; A61K 47/38;
    (Continued)

(56) References Cited

U.S. PATENT DOCUMENTS 4,294,829 A * 10/1981 Suzuki ................ A61K 9/0043
                                                    514/174
2007/0104791 A1* 5/2007 Popov ..................... A61P 11/02
                                                    424/488

FOREIGN PATENT DOCUMENTS

GB       2423711        9/2006
WO       2006040596     4/2006
WO       2015189579     12/2015

OTHER PUBLICATIONS

The pdf document "Marshfield clinic 2001" is a webpage from the Marshfield clinic at https://www.marshfieldclinic.org/specialties/allergies/allergies-allergic-and-non-allergic-rhinitis-frequently-asked-questions accessed Sep. 26, 2021, online since Jan. 31, 2001 according to Google (see pdf p. 1). (Year: 2001).*

* cited by examiner

*Primary Examiner* — David W Berke-Schlessel
*Assistant Examiner* — Trent R Clarke
(74) *Attorney, Agent, or Firm* — Nyemaster Goode, P.C.

(57) ABSTRACT

A nasal composition is provided comprising or consisting of a first composition part in the form of a liquid for nasal application to a patient in use, and a second composition part in the form of a powder for nasal application to the patient in use. The first and second composition parts are applied to the patient separately or together as required.

16 Claims, 8 Drawing Sheets

(51) Int. Cl.
*A61K 31/4174* (2006.01)
*A61K 9/00* (2006.01)
*A23L 33/10* (2016.01)
*A61K 9/16* (2006.01)
*A61M 11/00* (2006.01)
*A61M 15/08* (2006.01)

(52) U.S. Cl.
CPC .......... *A61K 9/0075* (2013.01); *A61K 9/0078* (2013.01); *A61K 9/1652* (2013.01); *A61K 47/38* (2013.01); *A61M 11/00* (2013.01); *A61M 15/08* (2013.01); *A23V 2002/00* (2013.01); *A61M 2202/04* (2013.01); *A61M 2202/064* (2013.01)

(58) Field of Classification Search
CPC .. A61M 11/00; A61M 15/08; A61M 2202/04; A61M 2202/064
See application file for complete search history.

Table 1. The visual analogue scale (VAS) assessments by patients' on days 1, 8 and 15 of nasal congestion, rhinorrhea, itching/sneezing and total nasal symptoms.

| Symptom | Mean baseline VAS (± SEM) | VAS & reduction (%) at 8 days | VAS & reduction (%) at 15 days |
|---|---|---|---|
| _Congestion_ | | | |
| Placebo | 56.6 ± 4.9 | 43.6 ± 5.7 23% ($P = 0.04$) | 47.2 ± 5.8 17% (N.S.) |
| HPMC | 65.0 ± 4.1 | 42.6 ± 6.4 35% ($P = 0.004$) | 36.2 ± 6.7 44% ($P < 0.001$) |
| Sig. of difference between groups | | N.S. | N.S. |
| _Rhinorrhoea_ | | | |
| Placebo | 61.9 ± 7.7 | 43.6 ± 5.7 39% ($P = 0.003$) | 47.7 ± 5.8 23% ($P = 0.04$) |
| HPMC | 59.7 ± 6.2 | 37.9 ± 6.9 36% ($P = 0.012$) | 32.5 ± 7.3 46% ($P = 0.013$) |
| Sig. of difference between groups | | N.S. | N.S. |
| _Itch/Sneezing_ | | | |
| Placebo | 27.7 ± 7.1 | 24.3 ± 5.9 12% (N.S.) | 21.2 ± 5.6 23% (N.S.) |
| HPMC | 32.8 ± 7.0 | 14.3 ± 4.6 56% ($P = 0.012$) | 8.5 ± 3.0 74% ($P = 0.013$) |
| Sig. of difference between groups | | N.S. | N.S. |
| _Total symptoms_ | | | |
| Placebo | 68.4 ± 5.1 | 39.6 ± 5.8 42% ($P < 0.001$) | 41.7 ± 5.7 39% ($P < 0.001$) |
| HPMC | 70.2 ± 5.2 | 43.7 ± 6.0 38% ($P = 0.002$) | 34.2 ± 6.5 51% ($P < 0.001$) |
| Sig. of difference between groups | | N.S. | N.S. |

Fig. 7

NASAL COMPOSITIONS AND METHOD OF USE THEREOF

This application is a continuation of U.S. Ser. No. 15/317,211 filed Dec. 8, 2016 which claims priority to GB1410250.3 filed Jun. 10, 2014, the disclosures of which are hereby incorporated by reference in its entirety.

BACKGROUND

The present invention relates to improvements to nasal compositions and to a method of use thereof.

Although the following description refers almost exclusively to a nasal decongestant composition and to a method of application thereof, it will be appreciated by persons skilled in the art that the present invention can be used for any nasal composition used for any purpose.

Nasal administration for delivery of drugs to a patient for either local or systemic effect is known. Examples of common nasally delivered drugs are decongestants and allergy treatments. The drug compositions are typically in the form of a liquid spray or drops containing at least one therapeutically active agent that is applied via spraying or locating droplets into a user's nasal cavity using a suitable dispenser, such as a pipette or dropper.

The nasal cavity is covered with a thin mucosa that has a good blood supply. A drug molecule can be transferred quickly from the nasal cavity across a single epithelial layer of the mucosa and directly into the systemic blood circulation of the patient without hepatic and intestinal metabolism. This allows the therapeutically active agent to have a rapid effect within the patient's body and provides an alternative route of application to oral administration or other administration forms. A problem associated with nasal administration of drug compositions in liquid form is that the liquid can flow out of the nasal cavity of the patient due to gravity and normal nasal clearance (i.e. via nasal secretions or mucociliary action) before it is absorbed through the nasal mucosa.

In an attempt to overcome the abovementioned problem, initial studies have been undertaken which show that application of a single mucoadhesive pharmaceutical solution with a decongestant contained therein have a greater and longer lasting effect in subjects with perennial allergic rhinitis than a standard commercially available decongestant solution without a mucoadhesive solution contained therein (Tzachev et al—Br J Chin Phamacol. January 2002: 53 (1): 107-109—" Comparison of the clinical efficacy of standard and mucoadhesive based nasal decongestants). However, the development Of any fixed formulation drug and mucoadhesive carrier is likely to be both expensive and time consuming. There is therefore still a need to develop a commercially available nasal composition that overcomes the problems of the prior art.

It is therefore an aim of the present invention to provide an improved nasal composition.

It is an aim of the present invention to provide a method of using an improved nasal composition.

It is a yet further aim of the present invention to provide a combination therapy for nasal application and a method of use thereof It is a yet further aim of the present invention to provide a kit of parts for a nasal composition and a method of use thereof.

SUMMARY

According to a first aspect of the present invention there is provided a nasal composition, said nasal composition comprising or consisting of a first composition part in the form of a liquid for nasal application to a patient in use, and a second composition part in the form of a powder for nasal application to the patient in use, said first and second composition parts applied to the patient separately or together as required.

The applicants have found that provision of the second powder composition part prolongs the contact time of the first liquid composition part in the nasal cavity with the nasal mucosa, thereby increasing the efficiency of the transfer of the liquid across the nasal mucosa in use. This in turn increases the efficacy of any agent or therapeutic agent that may be contained within the first liquid composition part. The method of action of the composition parts is thought to be as a result of the second powder composition part slowing down the clearance of the first liquid composition part due to the creation of weak and/or temporary bonds between one or more components of the first and second composition parts and/or between one or more components of the first and second composition parts and the nasal mucosa.

Thus, in one embodiment the second composition part is provided at such a dose, timing between delivery of the first and second composition parts and/or arrangement of the first and second composition parts so that the second composition part improves the mucoadhesive action of the first composition part relative to if the first composition part is given on its own.

Preferably alteration of the grade and/or concentration of the second composition part can be used to alter the mucoadhesive action of the first composition part, thereby making the clearance of the first liquid composition part from the nasal cavity relatively faster or slower.

In one embodiment the first liquid composition part includes or consists of any or any combination of one or more therapeutically active agents, a drug, a steroid, pharmaceutical product, decongestant, allergy therapy agent, herbal agent, homeopathic agent, food supplement, probiotic, airway dilator and/or the like.

Non-limiting examples of decongestants and non-limiting examples of the concentrations of the same that can be used for the first liquid composition part include Xylometazoline (i.e. 0.05% w/w), Oxymetazoline (i.e. 0.025-0.05% w/w) and/or the like.

An example of an anti-histamine that can be used for the first liquid composition part is Azelastine (and non-limiting examples of the concentration are 0.1% or 0.15% w/w) and/or the like.

Non-limiting examples of nasal steroids that can be used for the first liquid composition part include Mometasone furoate (and a non-limiting example of the concentration is 0.05% w/w), Fluticasone propionate (and a non-limiting example of the concentration is 88 mcg-440 mcg per dose), Fluticasone Furoate (and a non-limiting example of the concentration is 88 mcg-440 mcg per dose).

An example of an antimuscarinic that can be used for the first liquid composition part includes Ipratropium bromide (and a non-limiting example of the concentration is 34-500 mcg per dose).

An example of a combination anti-histamine and nasal steroid that can be used for the first liquid composition part includes Azelastine and Fluticasone propionate.

The dosages of the first liquid composition part are typically as per the recommended drug use guidelines for the patient in question and the disease state and/or condition being treated.

The first liquid composition part can be applied to the nasal cavity of a patient in the form of a liquid spray or as droplets using a suitable nasal dispenser, such as for example a nasal spray dispenser, a nasal pipette, nasal dropper and/or the like.

The second powder composition part can be applied to the nasal cavity of a patient as a result of a user inhaling the nasal powder using a suitable nasal dispenser, such as for example a squeeze bottle and/or the like. An example of a possible nasal applicator for the powder composition is disclosed in EP1368090, incorporated herein by reference. The powder dispenser typically includes a deformable bottle containing the powdered composition and which houses a dip tube. Application of a squeezing force on the sides of the bottle, using opposing fingers of a user, increases the internal pressure of the bottle when compared to atmospheric pressure. This results in an airflow that is channelled out of the bottle through the dip tube. This airflow entrains powdered material, releasing a restricted amount of the powdered material from the bottle.

Preferably the dispensing apparatus of the first and/or second composition parts dispenses a pre-defined dosage of liquid and powder respectively, thereby controlling the dosage of the composition parts to the user.

Preferably the dosage of the first and/or second composition parts are pharmaceutically effective and/or acceptable dosages.

In one embodiment the second powder composition part includes or consists of any or any combination of cellulose powder, Hydroxypropylmethylcellulose (HPMC) powder, one or more therapeutically active agents, pharmaceutical agents, steroid, drug, signalling agents, airway dilator agents, herbal agents, homeopathic agent, probiotics, food supplements and/or the like, such as for example any or any combination of a drug, decongestant, allergy therapy agent and/or the like. It can also contain a specific catalyst and/or an enhancer of a pro-drug contained in the first liquid composition.

Preferably the HPMC is a dry powder and is typically inert.

The term "therapeutically active agent" used herein is typically any active substance suitable for nasal administration or its inactive pro-drug to be subsequently activated.

The term "homeopathic" or "herbal" are used herein to refer to products derived from natural plant or mineral sources.

In one embodiment the therapeutic, homeopathic and/or herbal agent may have one or more of the following properties: antibacterial, antifungal, antiviral, antibiotic, immunomodulating, anti-inflammatory, anti-insomnia, cognitive enhancing or properties that affect cardiovascular function and/or the like.

Specific therapeutically active agents may include any or any combination of: aspirin, isoprenosine, acyclovir, St. John's Wort, valerian extract, ginkgo biloba extract, Vitamins, garlic, lime ginger, ellagic acid, Echinacea, Swedish flower pollen, black walnut hulls, lemongrass, wormwood, grapefruit seed extract, broccoli, digestive enzymes, hyaluronic acid, astralgus, rosehips, gentian, hypericum, horse chesnut, ginseng, green tea, phosphatidyl serine, phosphatidyl choline, citrus, pycnogenol, caffeine, quercitin, co-enzyme Q10, yarrow, tea tree, noni juice, lipase, fructo-oligosaccharide, inulin, black cumin or allicin, any mint variety, turmeric and/or the like.

The term "pharmaceutical agent" as used herein refers to an agent available only under prescription or that requires efficacy, toxicity and marketing approval from the Medicines and Healthcare Products Regulatory Agency before use.

In one embodiment the second composition part includes or consists of hydroxymethylcellulose (HPMC), an inert cellulose powder and/or the like. The HPMC or cellulose powder remains as a powder until it enters the patient's nasal cavity wherein it immediately turns to a gel like material on administration as it reacts with moisture present in the nasal tract.

In one embodiment the second composition part includes or consists of a cellulose powder with or without the presence of one or more other agents, therapeutically active agents, signalling agents, airway dilator agents, a specific catalyst and/or enhancer of a pro-drug contained in the first liquid composition and/or the like.

Preferably the second composition part includes or consists of a significant proportion of cellulose powder or HPMC powder therein. Further preferably the second composition part comprises at least 50% HPMC or cellulose powder, preferably at least 60, 70, 80, 90, 95, 97 or 99% HPMC or cellulose powder by total weight of the second composition part.

Preferably the dosage of the second composition part is between about 1 mg-10 mg per nostril of a patient. Further preferably the dosage is between about 2.5 mg-7.5 mg, between about 3-7 mg, between about 4-6 mg, or about 5 mg per nostril of a patient.

The first and/or second composition part is typically given over such time scales as recommended by a medical practitioner and/or until the condition being treated as been eradicated.

In one embodiment the second composition part is a HPMC powder composition as set out in EP1824450, incorporated herein by reference.

The HPMC or cellulose powder has a viscosity of approximately 10-20 Pa·s (Pascal Second) in a 2% aqueous solution at 20° C., preferably approximately 13-17 Pa·s, more preferably 14-16 Pa·s and most preferably 15 Pa·s. The viscosity is typically measured using a Ubbelohde viscometer.

Preferably the second composition is of a type sold under the brand name of NASALEZE®, NoAL®, NASAVAL, BOOTS ALLERGY BARRIER, ALERBLOCK, or other names as licensed by brand owners Nasaleze International Ltd. Products under these brand name are conventionally used as isolators to isolate contaminants and germs and prevent the same from entering the nasal mucosa of a patient. In the present invention the products are being used in a novel manner as sealants to seal a liquid applied to the nasal cavity before or after administration of the same.

In one embodiment the second composition part includes any or any combination of kali bichromium; a thickening agent such as gum or starch; a disintegrant, such as sodium glycolate or cross linked povidone, a release agent such as magnesium stearate; an emulsifying agent, a surfactant, anti-caking agents, granulating agents preservatives, colourants and/or the like.

In one embodiment the second composition part includes a signalling or flavouring agent that can provide the patient with a pleasant sensory feedback upon use, which allows the patient to recognise that administration of the second composition part has taken place. The signalling agent can include any or any combination of mint, menthol, spearmint, any mint variety, turmeric, lemon, lime, peppermint, eucalyptus, lavender, citrus, strawberry, capsaicin and/or the like.

In one embodiment the signalling agent comprises up to 50% of the second composition part, preferably up to 40%, 30%, 20%, 10%, 5%, 2%, 1%, 0.5% or 0.25% by total weight of the second composition part.

In one embodiment the second composition part is administered to the patient prior to or just prior to administration of the first composition part.

In one embodiment the first composition part is administered to the patient prior to or just prior to administration of the second composition part.

In one embodiment the first composition part and the second composition part are administered simultaneously or substantially simultaneously.

Preferably the first and second composition parts, irrespective of the order in which they are administered, are administered sequentially one after another, and preferably immediately after each other. Further preferably the second composition part is administered last or second in the sequence.

In one embodiment the first and second composition parts are administered less than or equal to 5 minutes after each other; preferably less than or equal to 2 minutes after each other; further preferably less than or equal to 1 minute after each other; and yet further preferably less than or equal to 30 seconds after each other, 20 seconds, 10 seconds, 5 seconds, 1 second after each other.

In one embodiment the composition can include or consist of a third composition part and/or one or more further composition parts in addition to the first and second composition parts. The third and/or further composition parts can be administered nasally in any required order with the first and second composition parts, although it is preferred that the second composition part is administered last in the sequence. The third and/or further composition parts can be administered immediately before, between or after the first and second composition parts, a predetermined time period thereafter, substantially simultaneously to and/or the like. An example of a third composition part that can be given in combination with a first composition part is use of an anti-histamine with a nasal corticosteroid, such as for example, Azelastine and Fluticasone Propionate.

In one embodiment the composition consists of the first composition part and the second composition part to the exclusion of any other composition part.

In one embodiment the first composition part, the second composition part and/or the third and/or further composition parts are stand alone, independently applied, composition parts that are not mixed together or come into contact with each other until application into the nasal cavity of a patient.

The composition of the present invention could be used to provide a local effect in the nasal tract of a patient or could be absorbed into the blood stream and used to provide a systemic effect in a patient as required.

According to one independent aspect of the present invention there is provided a nasal composition, said nasal composition comprising a first composition part for nasal application to a patient in use, and at least a second composition part for nasal application to a patient in use, said first and second composition parts applied separately or together as required, the second composition part arranged so as to increase the mucoadhesion of the one or more components of the first composition with the nasal mucosa of a patient in use.

Preferably the first composition part is in the form of a liquid.

Preferably the second composition part is in the form of a powder.

According to one aspect of the present invention there is provided a combined nasal therapy, said combined nasal therapy comprising a first composition part in the form of a liquid for nasal application to a patient in use, and a second composition part in the form of a powder for nasal application to a patient in use, said first and second composition parts applied separately or together as required.

According to one aspect of the present invention there is provided a kit of parts for a nasal composition, said kit of parts comprising a first composition part in the form of a liquid for nasal application to a patient in use, and a second composition part in the form of a powder for nasal application to a patient in use, said first and second composition parts applied separately or together as required.

According to one aspect of the present invention there is provided a method of treating a patient with a nasal composition. The treatment can be effective for the diseases relating to the respiratory tract, allergic ailments, rhinitis, the upper respiratory tract, the lower respiratory tract of a patient, as a decongestant, rhinovirus, common cold and/or the like.

According to one aspect of the present invention there is provided a composition for the manufacture of a medicament for the treatment of a disease or illness relating to the respiratory tract, allergic ailments, rhinitis, the upper respiratory tract, the lower respiratory tract of a patient, said nasal composition comprising or consisting of a first composition part in the form of a liquid for nasal application to a patient in use, and a second composition part in the form of a powder for nasal application to the patient in use, said first and second composition parts applied to the patient separately or together as required.

An embodiment of the present invention will now be described with reference to the accompanying figures, wherein:

BRIEF DESCRIPTION OF THE DRAWINGS

FIG. 7 is a table showing the VAS assessments by patients on days 1, 8, and 15 of nasal congestion, rhinorrhea, itching/sneezing and total nasal symptoms.

DETAILED DESCRIPTION

A one centre clinical study was undertaken to determine the effectiveness of a nasal composition which is based on the sequential application of two commercially available composition parts. The first composition part is in the form of an existing commercially available non-adhesive decongestant liquid formulation and the second composition part is in the form of an existing commercially available cellulose containing powder to determine if the second composition part can "seal" the non-adhesive decongestant formulation in place within the nasal cavity of a patient.

The proposed mode of operation of the cellulose containing powder is that upon contact of the cellulose containing powder with the nasal mucosa of a patient, the powder converts into an adhesive gel, which slows down the nasal clearance of the first composition part with subsequent enhancement of the therapeutically active decongestant agent contained in the first composition part.

Method

The first composition part used was a decongestant liquid product called AFRIN® (distributed by Merck Consume Care, Inc) with the decongestant active agent Oxymethazoline 0.05% contained therein. The second composition part used was a micronized methylcellulose powder called NoAL (supplied by Nasaleze Ltd), licensed for the treatment of allergic rhinitis. The first and second composition parts were administered by the patient into their nasal cavity immediately after each other. The dosage regime was 1 puff/squirt of AFRIN immediately followed by 1 puff/squirt of NoAL once a day for 7 days and then only.

The double-blind, randomised, placebo-controlled study contained 40 patients suffering from moderately severe to severe perennial allergic rhinitis, with prominent nasal congestion. Defective nasal barrier function is implicated in allergic rhinitis, resulting in persistent inflammation and clinical symptoms, among which nasal congestion plays a prominent role. The study was performed out of the pollen season, between November and January. Inclusion criteria also included a positive skin prick test (wheal>3 mm diameter) to at least one of a panel of perennial allergens. Exclusion criteria encompassed individuals with seasonal allergic rhinitis or nasal polyposis; patients with serious chronic co-morbidities; with flu-like symptoms during the past 30 days; pregnant or lactating women and individuals unable to give informed consent were excluded.

Figure 1A:
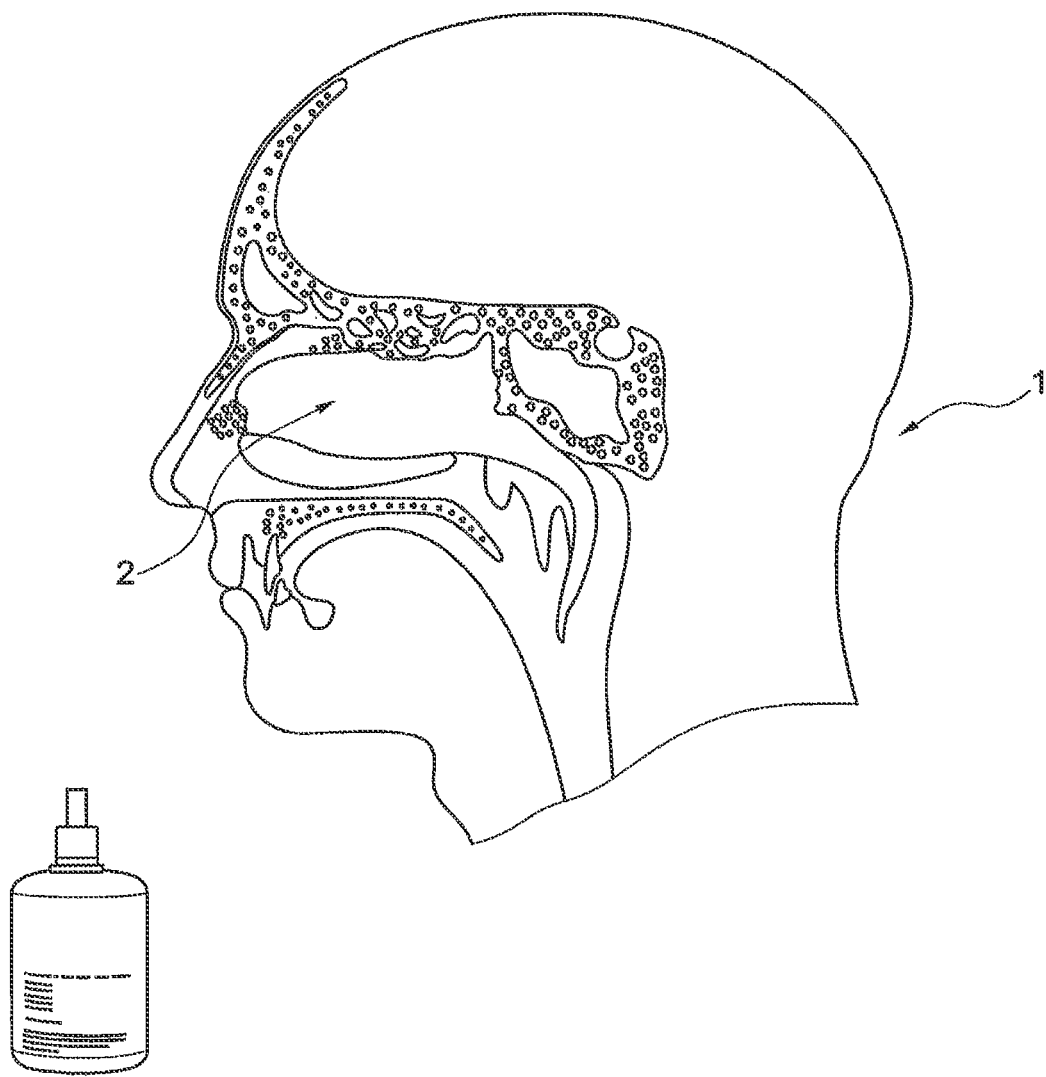
FIGS. 1a and 1b shows a cross sectional pictorial view taken through a patient's nasal cavity and upper respiratory tract 1 illustrating post use of AFRIN® only (distributed by Merck Consume Care, Inc) with the decongestant active agent Oxymethazoline contained therein, shown by reference 2, and post use of AFRIN®+NoAL® (supplied by Nasaleze Ltd) in combination, shown by reference 4 respectively. The darker shading of reference 4 shows a sealant effect created by use of the NoAL® in combination with the AFRIN® compared to the use of AFRIN® alone.
Figure 1B:
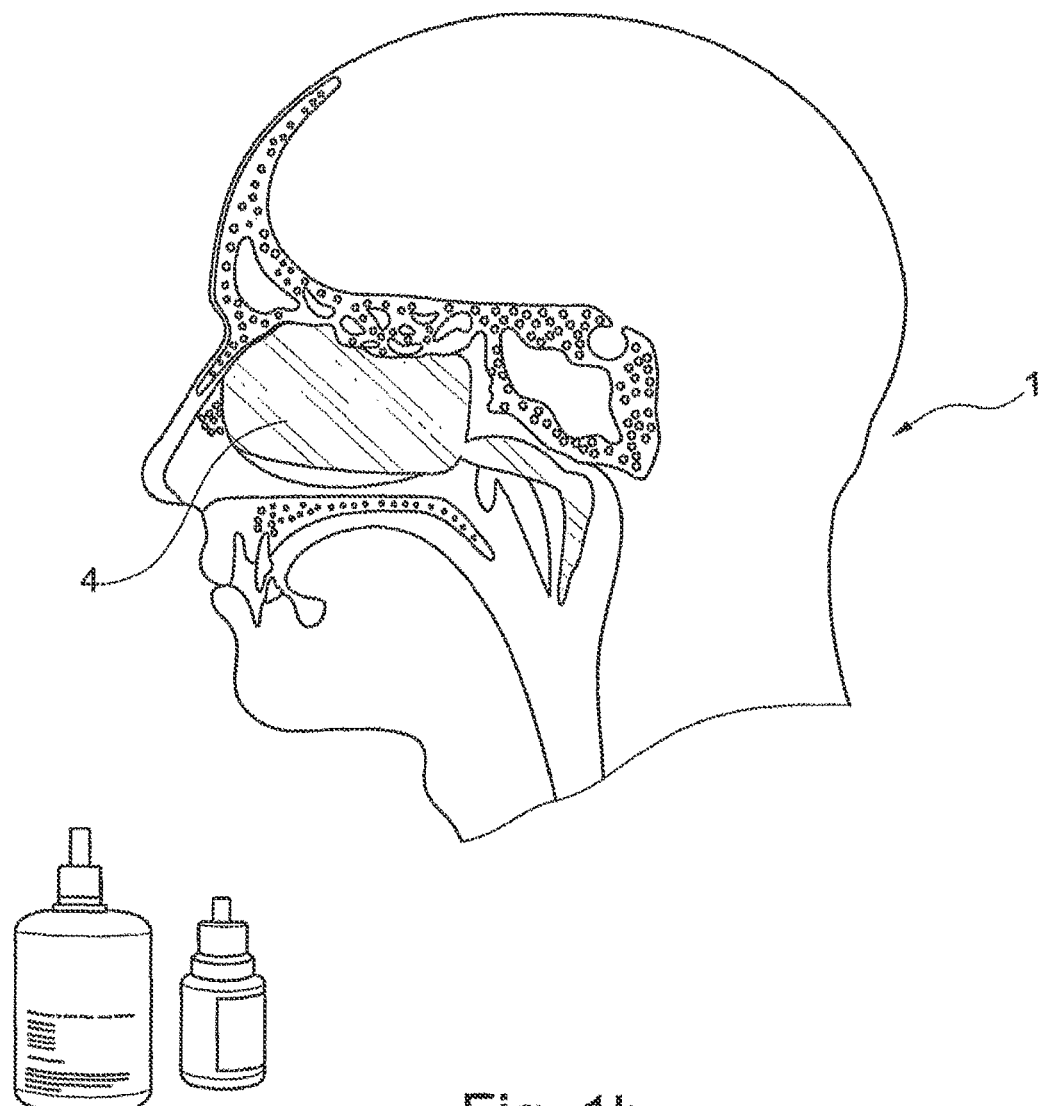
Figure 2:
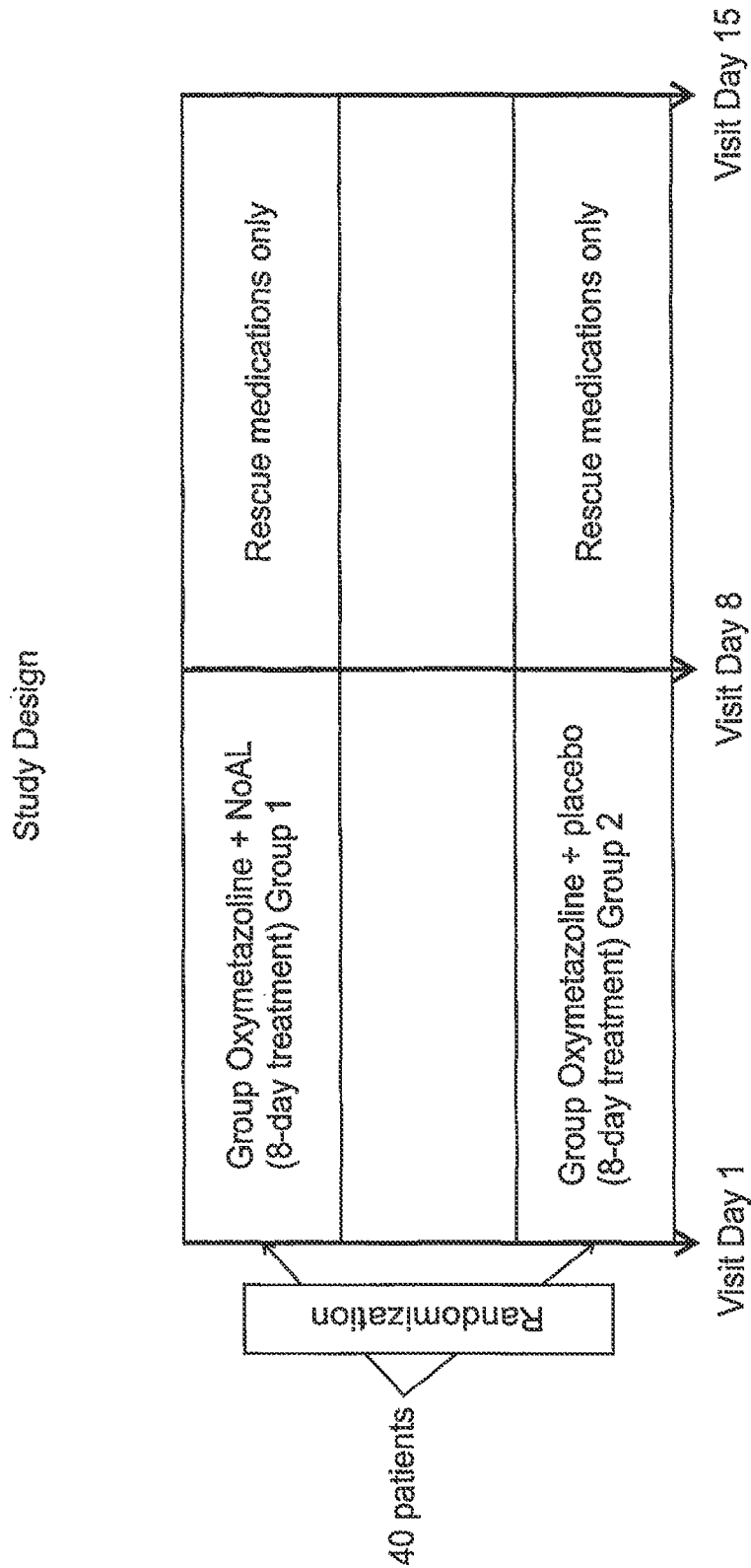
FIG. 2 shows a simplified illustration of a study design undertaken to show the effects of 40 patients used in the clinical study.

Half of the patients (20 patients) were selected at random for administration of a Group 1 composition, which was the administration of the AFRIN (Oxymetazoline nasal spray, 0.05%) and the NoAL (cellulose/HPMC powder), and half of the patients (20 patients) were selected at random for administration of a Group 2 composition, which was the administration of the AFRIN (Oxymetazoline) and a placebo in the form of a lactose powder, as shown in FIG. 2. The group 1 and group 2 compositions were administered to the patients on day 1 and the patients were tested on day 1 after administration of the composition, at day 8 and at day 15. The group 1 and group 2 compositions were administered regularly on a daily basis between day 1 and day 8 by the patient. Rescue medications only were prescribed to the patients between day 8 and day 15 with the placebo and Oxymetazoline and NoAL no longer given.

Figure 3:
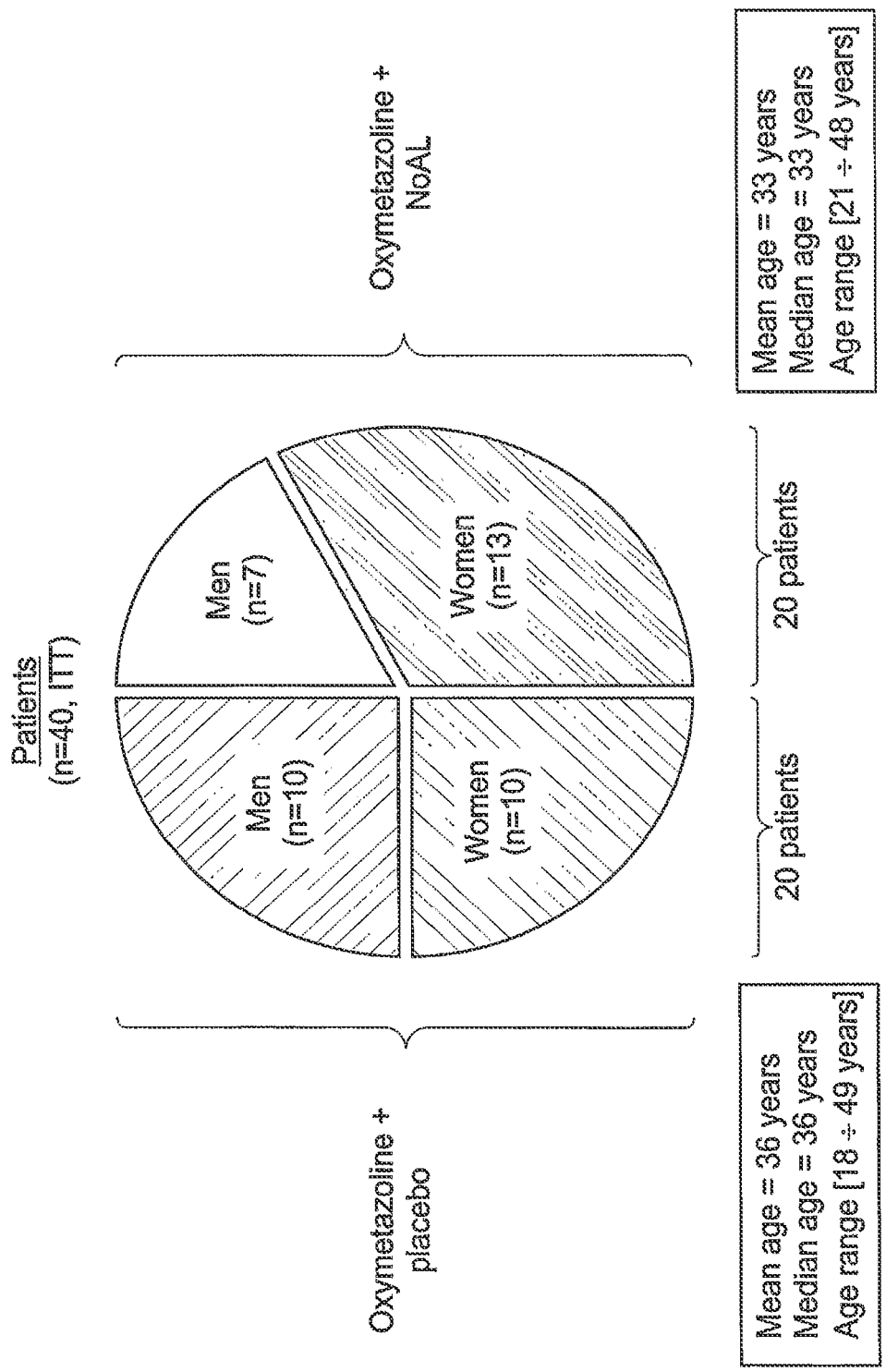
FIG. 3 shows a simplified illustration of the age and gender distribution of patients used in the clinical study shown in FIG. 2.

Of the patients used in the study, 10 of the group 1 patients were male and 10 of the group 1 patients were female; 7 of the group 2 patients were male and 13 of the group 2 patients were female. The age range of the group 1 patients was 18-49 years old, with a mean age of 36 years and a median age of 36 years. The age range of the group 2 patients was 21-48 years old, with a mean age of 33 years and a median age of 33 years, as shown in FIG. 3.

The parameters measured in the study for each patient at day 1, 8 and 15 included peak expiratory nasal flow (PNIF) using PNIF meters (In-Check Nasal, Clement Clarke International Ltd, Harlow, Essex, UK) which is a measure of respiratory function; a saccharine test; and subjective symptoms were measured using a visual-analogue scale (VAS) and using symptom scores of 0-3 in diaries. Overall discomfort due to allergic rhinitis symptoms were recorded during visits on a 10 cm VAS ranging from "no nasal symptoms" at 0 cm to "worst nasal symptoms" at 10 cm. Patients also rated their stuffiness, rhinorrhea, itching and sneezing by a symptom score between 0 (none) and 3 (worst). From this, the total nasal symptom score (TNSS) was calculated. The PNIF, L/min was measured on day 1 immediately before drug administration and at minutes 1, 5, 15, 30, 60, 120, 180, 240, 300 and 360 thereafter and the areas under the curve were analyzed. Similar measurements of PNIF were made on day 8, and a single measurement was taken on day 15. The saccharine test is a measure of nasal mucociliary clearance and involves placing a small particle of saccharine approximately 1 cm behind the anterior end of the inferior turbinate. In the presence of normal mucociliary action, the saccharin will be swept backwards to the patient's nasapharynx and a sweet taste is perceived by the patient. Failure of the patient to detect a sweet taste within 10-20 minutes signifies delayed mucociliary clearance.

Statistical Analyses

PNIF values were distributed normally and differences within groups analysed using Student's t-test for paired data and between groups Student's t-test for unpaired data. As the number of times patients resorted to rescue medication was not normally distributed, these results were given as median (25-75% range) and group differences assessed using the Mann-Whitney U test. All tests were two tailed and the threshold for statistical significance was set to P<0.05.

Results

Out of the 40 patients recruited in to the study, 2 dropped out from the test treatment group, 1 for non-compliance and the other for a headache; and 2 dropped out from the placebo group, 1 for concomitant disease and the other for a severe reaction to a cat. The remaining 36 patients completed all 3 visits and were included in the final analysis.

Figure 4:
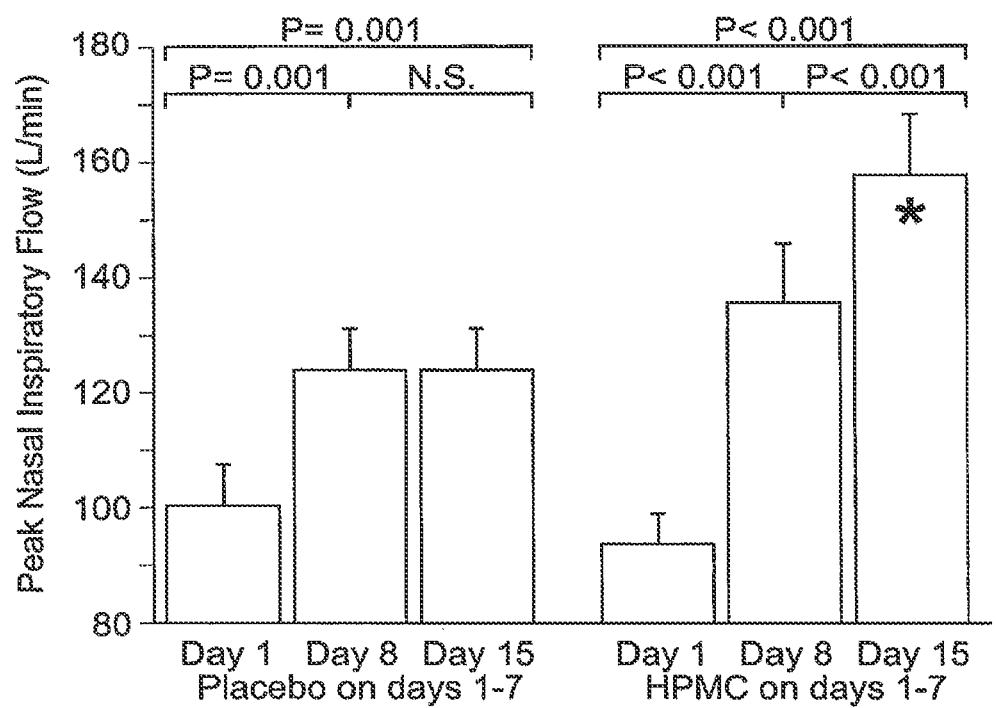
FIG. 4 is a graph showing the baseline peak expiratory nasal flow (PNIF) (L/min) values at days 1, 8 and 15 of the study.

FIG. 4 shows a graph of, the mean PNIF values at the start of the study (day 1), after 7 days treatment with HPMC powder or placebo (day 8) and after a further 7 days of only rescue medication (day 15). Each group contains results from 18 individuals. Significance values were calculated using Student's t-test for paired data. *indicated that the baseline PNIF of the HPMC treated patients at day 15 were significantly (P=0.014) greater than that of the placebo treated patients. The value was calculated using Student's t-test for unpaired data.

The results in the HPMC group showed a 26% (P<0.001) in PNIF at day 8 and a further 21% increase P<0.001) at day 15. The total increase in PNIF between days 1 and 15 was 53% (P<0.001). In the placebo group there was a 24% in PNIF (P<0.001) at day 8 but no further increase at day 15. There was no significant difference between groups on days 1 and 8, but the PNIF of the HPMC group was 26% greater (P=0.014) than that of the placebo group on day 15.

Figure 5:
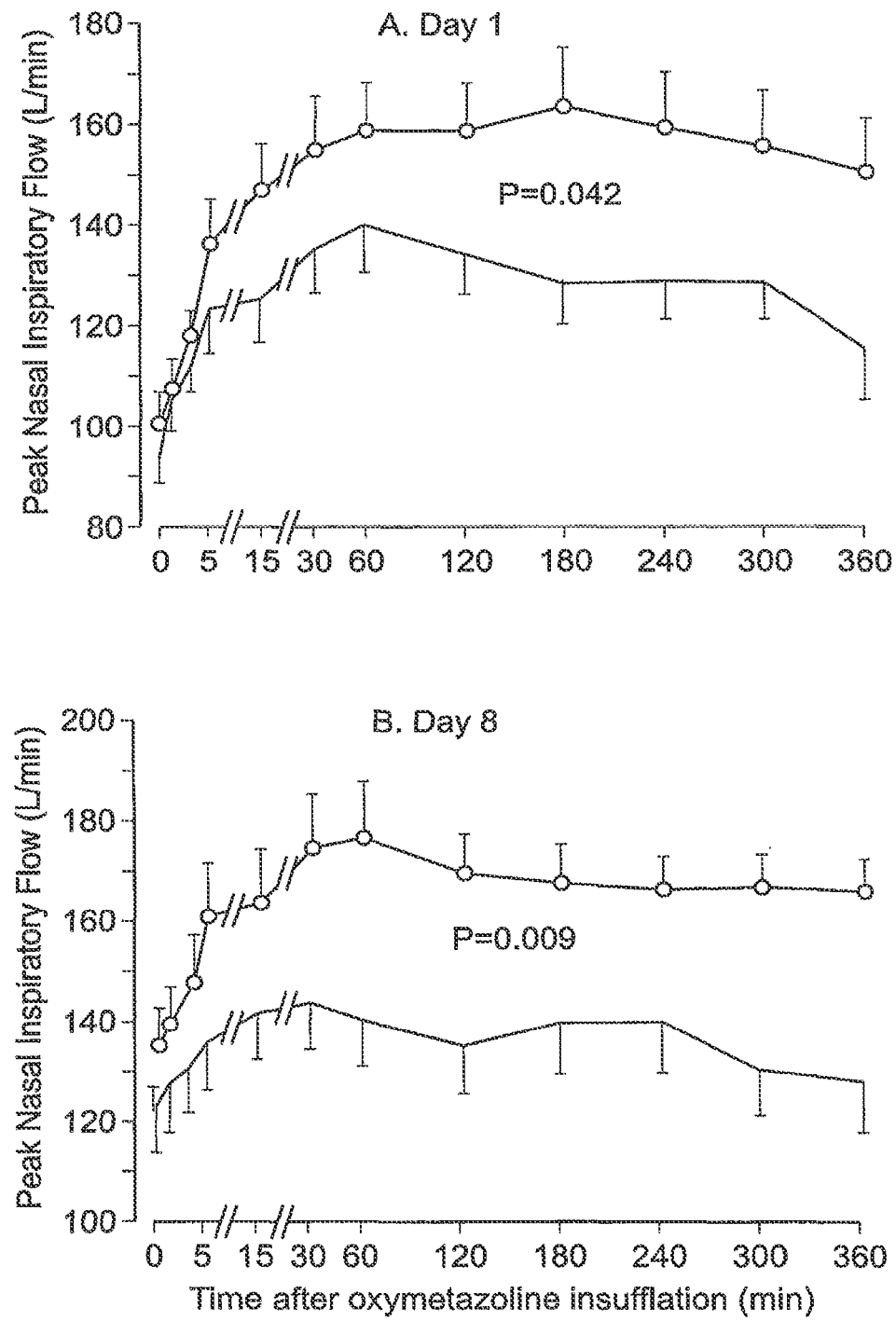
FIG. 5 is a graph showing the peak expiratory nasal flow (PNIF) (L/min) values following insufflation of oxymetazoline on A. day 1 and B. day 8.

FIG. 5 shows the PNIF values following insufflation of oxymetazoline on A. day 1 and B. day 8. The dots are the HPMC treated patients and the dots with a cross are the placebo group. Each group contains results from 18 individuals. Significance values were calculated using Student's t-test for unpaired data. On both days the effects of oxymetazoline were greater in patients also inhaling HPMC compared with the placebo group. On day 1, the area under the curve (AUC) for the 360 minutes of observations for oxymetazoline was 20% greater in patients receiving HPMC compared with those receiving the placebo (56,366+/−14,910 L·min/min vs 46,818+/−12,080 L·min/min, P=0.042). On day 8 AUC for oxymetazoline was 23% greater in the HPMC group than the placebo (60,855+/−13691 L·min/min vs 49,350+/−11211 L·min/min, P=0,009).

Figure 6:
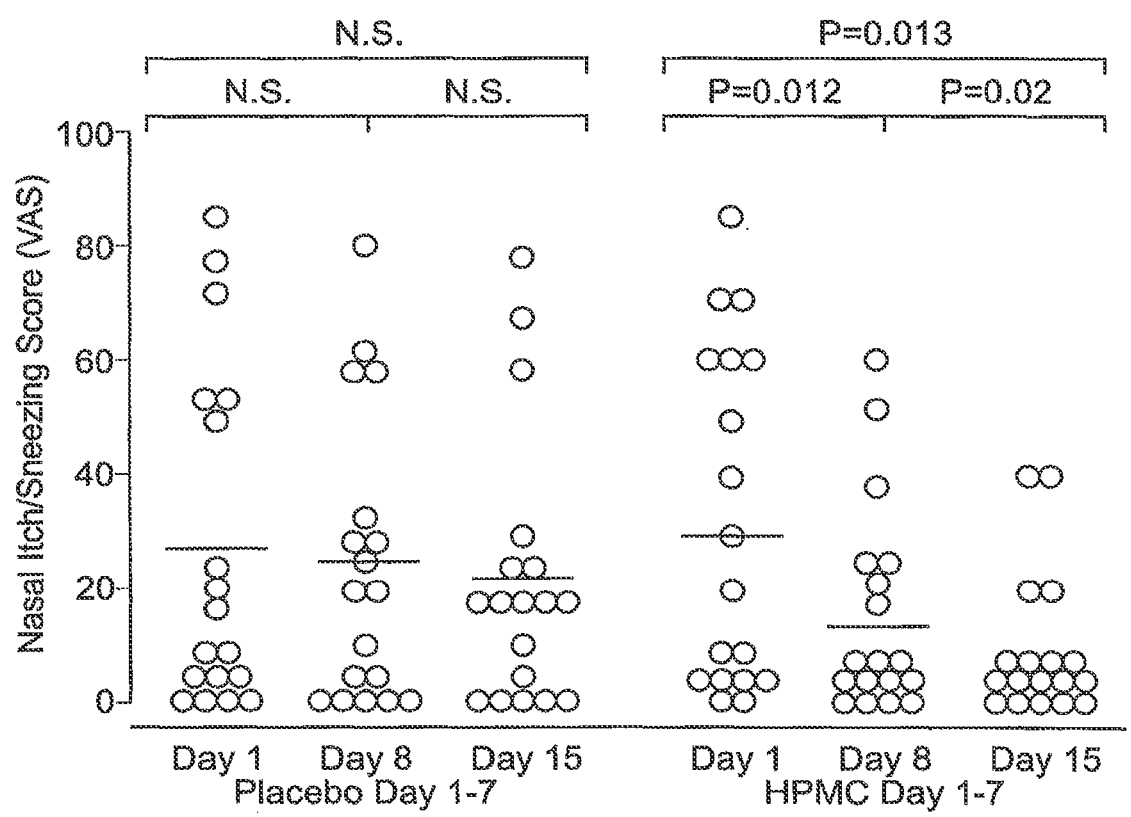
FIG. 6 shows the nasal itch/sneezing VAS scores on days 1, 8 and 15 of the study.

FIG. 6 shows the nasal itch/sneezing VAS scores on day 1, 8 and 15 of the study. The darkly shaded dots are the Placebo treated patients and the lightly shaded dots at the HPMC treated patients. Each group contains results from 18 individuals. Significance values were calculated using Student's t-test for paired data. There were no statistically significant differences between groups.

The VAS assessments by patients on days 1, 8 and 15 of nasal congestion, rhinorrhea, itching/sneezing and total nasal symptoms are shown in Table 1 of FIG. 7. In the placebo group, there were significant improvements in nasal congestion, rhinorrhea and total nasal symptoms at day 8 but little or no further improvement thereafter. In the HPMC treated group there were similar improvements in these parameters at day 8. However, in this group these improvements appeared to continue up to day 15. With total nasal symptoms the improvement between days 8 and 15 was statistically significant (P=0.006). There were no statistically significant differences between groups. A similar pattern of results was obtained from analysis of patients' diaries on days 1, 8 and 15 of the study.

Of special mention is nasal itching/sneezing. With this symptom there was no significant improvement in the placebo group. However, in the HPMC treated group there were significant improvements of 56% (P=0.012) and 74% (P=0.013) at days 8 and 15 respectively. Also, the improvement between days 8 and 15 was statistically significant (P=0.02). However, the differences between the treatment groups failed to reach statistical significance, mainly because of the numbers of patients giving low itch/sneezing scores at all times (see FIG. 6).

The median (with 25 and 75% range) numbers of times patients resorted to escape medication, puffs of oxymetazoline, during days 8-15 of the study were 8.5 (1-15.5) for the HPMC group and 16 (11.5-16) for the placebo group. There was a wide variability between the patients which precluded the difference between groups being statistically significant (P=0.076). However, 13 of the 18 patients who received the placebo on days 1-7 took more than 2 puffs of oxymetazoline per day compared with only 5 HPMC treated patients (P=0.04, Fisher's exact test).

The conclusions of the study showed that use of micronized methylcellulose powder (HPMC) enhanced the decongestant effect of nasal oxymetazoline in patients with perennial allergic rhinitis. One week of regular treatment with nasal oxymetazoline and HPMC augmented the nasal patency and this effect carried over for at least one further week after its discontinuation. This carry over effect may be as a result of the HPMC augmenting the mucosal barrier in allergic rhinitis.

The Applicants hypothesise that there are two possible mechanisms by which HPMC may act to enhance the effects of oxymetazoline therapy. The first is a purely physical one. As HPMC was insufflated immediately after oxymetazoline, the formation of a gel layer above the decongestant would be likely to reduce its clearance from the nasal mucosa and thereby increase its effectiveness. Such effect would occur even with the first dose as was seen on day 1 of the study. The second mechanism would be for HPMC to create an improved barrier to allergen penetration into the nasal mucosa. In the longer term, it would reduce the inflammatory events of the mucosal barrier thereby reducing nasal reactivity. The activity is evidenced particularly by the increased baseline PNIF, an index of nasal congestion, up to 15 days in the HPMC treated group.

Although the study was undertaken only in respect of patients suffering from perennial allergic rhinitis, the results of the study suggest that a similar effect could be found in patients suffering from other respiratory and/or allergy complaints.

The invention claimed is:

1. A method of treating a patient with nasal congestion comprising: administering intranasally to a patient a composition comprising a first composition part and a second composition part, whereby the first composition part is in the form of a liquid decongestant, said liquid decongestant comprising from 0.025-0.05% w/w oxymetazoline, followed by administering intranasally to the patient the second composition part, said second composition part comprising hydroxypropylmethylcellulose (HPMC) powder, and wherein the patient is administered the first and second composition parts daily for seven days, followed by no administration of the first and second composition parts for at least seven days.

2. The method according to claim 1 wherein the first composition part is administered as a dose comprising a single puff or squirt.

3. The method according to claim 2 wherein the second composition part is administered as a dose comprising a single puff or squirt.

4. The method according to claim wherein the second composition part includes at least 50% HPMC powder, or wherein the second composition part includes at least 60, 70, 80, 90 or 99% HPMC powder by total weight of the second composition part.

5. The method according to claim wherein the dosage of the second composition part is between 1 mg -10 mg per nostril of a patient, or wherein the dosage of the second composition part is between 2.5 mg -7.5 mg, between 3-7 mg, between 4-6 mg or about 5 mg per nostril of a patient.

6. The method according to claim 1, wherein said HPMC powder has a viscosity of 10-20 Pas in a 2% aqueous solution at 20° C., or wherein the HPMC powder has a viscosity of 13-17 Pas, 14-16 Pas or 15 Pas.

7. The method according to claim 1, wherein the second composition part further includes one or more ingredients selected from the group consisting of kali bichromicum, a thickening agent, gum, starch, a disintegrant, sodium glycolate, a crosslinked povidone, a release agent, magnesium stearate, an emulsifying agent, a surfactant, anticaking agents, granulating agents, preservative, colorant, a signalling agent that can provide the patient with a pleasant sensory feedback upon use, and a flavouring agent that can provide the patient with a pleasant sensory feedback upon use.

8. The method according to claim 1, wherein the second composition part further includes a signalling agent, wherein the signalling agent is one or more agents selected from the group consisting of mint, menthol, spearmint, any mint variety, turmeric, lemon, lime, peppermint, eucalyptus, strawberry, lavender, citrus, and capsaicin.

9. The method according to claim 1, wherein the second composition part further includes a signalling agent, wherein the signalling agent comprises up to 50% of the second composition part.

10. The method according to claim 1 wherein the first composition part is applied to the patient immediately followed by the second composition part.

11. A method of treating a patient with nasal congestion comprising: administering intranasally to a patient a first composition comprising 0.025-0.05% w/w oxymetazoline followed by administering intranasally to the patient a second composition comprising hydroxypropylmethylcellulose (HPMC) powder, and wherein the patient is administered the first and second compositions daily for seven days, followed by no administration of the first and second compositions for at least seven days, whereby the HPMC powder has a viscosity of 10-20 Pas in a 2% aqueous solution at 20° C., or wherein the HPMC powder has a viscosity of 13-17 Pas, 14-16 Pas or 15 Pas.

12. The method according to claim 11 whereby the second composition is administered less than five minutes after the first composition is administered.

13. The method according to claim 12 whereby the second composition is administered immediately after the first composition is administered.

14. A method of treating a patient with nasal congestion comprising: administering intranasally to a patient a first composition in the form of a liquid decongestant comprising 0.025-0.5% w/w oxymetazoline followed by administering intranasally to the patient a second composition comprising hydroxypropylmethylcellulose (HPMC) powder, and a third composition comprising a corticosteroid; and wherein the patient is administered the first and second compositions daily for seven days, followed by no administration of the first and second compositions for at least seven days.

15. The method according to claim 14 whereby the third composition is administered immediately before, between or after the first and second compositions.

16. The method according to claim 14 whereby the second composition is administered after the first and third compositions.

* * * * *